US007678775B2

(12) United States Patent
Kretzler et al.

(10) Patent No.: US 7,678,775 B2
(45) Date of Patent: Mar. 16, 2010

(54) ILK INHIBITORS FOR THE TREATMENT OF RENAL DISEASE

(75) Inventors: Matthias Kretzler, Ann Arbor, MI (US); Patricia Logan, Vancouver, CA (US)

(73) Assignee: QLT Inc., Vancouver, British Columbia (CA)

( * ) Notice: Subject to any disclaimer, the term of this patent is extended or adjusted under 35 U.S.C. 154(b) by 0 days.

(21) Appl. No.: 11/855,884

(22) Filed: Sep. 14, 2007

(65) Prior Publication Data

US 2008/0003217 A1 Jan. 3, 2008

Related U.S. Application Data

(62) Division of application No. 10/497,285, filed as application No. PCT/CA02/01819 on Nov. 26, 2002.

(60) Provisional application No. 60/335,130, filed on Nov. 30, 2001.

(51) Int. Cl.
*A61K 31/70* (2006.01)
*C12Q 1/68* (2006.01)

(52) U.S. Cl. .................. 514/44; 514/1; 514/2; 514/4; 434/130.1

(58) Field of Classification Search ................ None
See application file for complete search history.

(56) References Cited

U.S. PATENT DOCUMENTS

| 6,001,622 A | 12/1999 | Dedhar et al. |
| 6,013,782 A | 1/2000 | Dedhar et al. |
| 6,177,273 B1 | 1/2001 | Bennett et al. |
| 6,214,813 B1 | 4/2001 | Zhang et al. |

FOREIGN PATENT DOCUMENTS

WO 97/23625 7/1997

OTHER PUBLICATIONS

Adler, S., et al., "Alteration of Glomerular Permeability to Macromolecules Induced by Cross-linking of β1 Integrin Receptors," Am. J. Pathol. 149(3):987-96, Sep. 1996.
Bariety, J., et al., "Posttransplantation Relapse of FSGS is Characterized by Glomerular Epithelial Cell Transdifferentiation," J. Am. Soc. Nephrol. 12(2):261-74, Feb. 2001.
Bariety, J., et al., "Podocytes Undergo Phenotypic Changes and Express Macrophagic-Associated Markers in Idiopathic Collapsing Glomerulopathy," Kidney Int. 53(4):918-25, Apr. 1998.
Beck, K., et al., "Downregulation of Integrin-linked Kinase mRNA Expression by Nitric Oxide in Rat Glomerular Mesangial Cells," Life Sci. 69(25-26):2945-55, Nov. 9, 2001.
Boute, N., et al., "NPHS2, Encoding the Glomerular Protein Podocin, is Mutated in Autosomal Recessive Steroid-resistant Nephrotic Syndrome," Nat. Genet. 24(4):349-54, Apr. 2000.
Coimbra, T., et al., "Early Events Leading to Renal Injury in Obese Zucker (fatty) Rats with Type II Diabetes," Kidney Int. 57(1):167-82, Jan. 2000.

Colucci-Guyon, E., et al., "Mice Lacking Vimentin Develop and Reproduce without an Obvious Phenotype," Cell 79 (4):679-94, Nov. 18, 1994.
Guo, L., et al., "The Distribution and Regulation of Integrin-linked Kinase in Normal and Diabetic Kidneys," Am. J. Pathol. 159(5):1735-42, Nov. 2001.
Haltia, A., et al., "mRNA Differential Display Analysis of Nephrotic Kidney Glomeruli," Exp. Nephrol. 7(1):52-8, Jan.-Feb. 1999.
Hannigan, G., et al., "Regulation of Cell Adhesion and Anchorage-dependent Growth by a New β1-integrin-linked Protein Kinase," Nature 379(6560):91-6, Jan. 4, 1996.
Heid, C., et al., "Real time Quantitative PCR," Genome Res. 6(10):986-94, Oct. 1996.
Huttunen, N., et al., "Glomerular Basement Membrane Antigens in Congenital and Acquired Nephrotic Syndrome in Childhood," Nephron. 16(6):401-14, 1976.
Jones, C., et al., "Serum Creatinine Levels in the US Population: Third National Health and Nutrition Examination Survey," Am. J. Kidney Dis. 32(6):992-9, Dec. 1998.
Kaplan, J., et al., "Mutations in ACTN4, Encoding Alpha-actinin-4, Cause Familial Focal Segmental Glomerulosclerosis," Nat. Genet. 24(3):251-6, Mar. 2000.
Kestilä, M., et al., "Positionally Cloned Gene for a Novel Glomerular Protein—nephrin—is Mutated in Congenital Nephrotic Syndrome," Mol. Cell. 1(4):575-82, Mar. 1998.
Kreidberg, J., et al.,"Alpha 3 Beta 1 Integrin has a Crucial Role in Kidney and Lung Organogenesis," Development 122 (11):3537-47, Nov. 1996.
Kretzler, M., et al., "Integrin-linked Kinase as a Candidate Downstream Effector in Proteinuria," FASEB J., 15 (10):1843-5, Aug. 2001.
Kretzler, M., "Regulation of Adhesive Interaction Between Podocytes and Glomerular Basement Membrane," Microsc. Res. Tech. 57(4):247-53, May 15, 2002.
Kretzler, M., et al., "Novel Mouse Embryonic Renal Marker Gene Products Differentially Expressed During Kidney Development," Am. J. Physiol. 271(3 Pt 2):F770-7, Sep. 1996.
Kretzler, M., et al., "Integrin Linked Kinase Induction by Podocyte Damage in Vivo and Vitro," Kidney & Blood Pressure Research 21(2-4):145, 1998.
Mundel, P., et al., "Rearrangements of the Cytoskeleton and Cell Contacts Induce Process Formation during Differentiation of Conditionally Immortalized Mouse Podocyte Cell Lines," Exp. Cell Res. 236(1):248-58, Oct. 10, 1997.

(Continued)

*Primary Examiner*—Sean R McGarry
(74) *Attorney, Agent, or Firm*—Seed IP Law Group PLLC

(57) ABSTRACT

The invention relates to the treatment of renal diseases using modulators of integrin linked kinase. Methods of treatment as well as therapeutic agents including antisense, small molecules, catalytic peptides and antibodies are disclosed. The agents of the invention may also be used in combination with traditional therapies for renal disease including ACE inhibitors. An advantage of the invention is that it treats one of the causes of renal disease, rather than just ameliorating symptoms, and can help prevent the progression of renal disease to the point of acute renal failure.

24 Claims, No Drawings

OTHER PUBLICATIONS

Neugarten, J., et al., "Role of Macrophages and Colony-stimulating Factor-1 in Murine Antiglomerular Basement Membrane Glomerulonephritis," J. Am. Soc. Nephrol. 5(11):1903-9, May 1995.

Novak, A., et al., "Cell Adhesion and the Integrin-linked Kinase Regulate the LEF-1 and β-catenin Signaling Pathways," Proc Natl Acad Sci U S A. 95(8):4374-9, Apr. 14, 1998.

O'Meara, Y., et al., "Nephrotoxic Antiserum Identifies a β1-integrin on Rat Glomerular Epithelial Cells," Am. J. Physiol. 262(6 Pt 2):F1083-91, Jun. 1992.

Radeva, G., et al., "Overexpression of the Integrin-linked Kinase Promotes Anchorage-Independent Cell Cycle Progression," J. Biol. Chem. 272(21):13937-44, May 23, 1997.

Sanai, T., et al., "Expression of Cytoskeletal Proteins During the Course of Experimental Diabetic Nephropathy," Diabetologia 43(1):91-100, Jan. 2000.

Schadde, E., et al., "Expression of Chemokines and their Receptors in Nephrotoxic Serum Nephritis," Nephrol. Dial. Transplant 15(7):1046-53, Jul. 2000.

Schroppel, B., et al., "Analysis of Mouse Glomerular Podocyte mRNA by Single-cell Reverse Transcription-polymerase Chain Reaction," Kidney Int. 53(1):119-24, Jan. 1998.

Shankland, S., et al., "Differential Expression of Cyclin-dependent Kinase Inhibitors in Human Glomerular Disease: Role in Podocyte Proliferation and Maturation," Kidney Int. 58(2):674-83, Aug. 2000.

Teixeira, V., et al., "Integrin Linked Kinase (ILK) Modulates Podocyte Phenotype and Cell Adhesion Through Interaction with Wnt Signaling Pathway Components," Kidney & Blood Pressure Research 23(3-5):231, 2000.

Terzi, F., et al., "Reduction of Renal Mass is Lethal in Mice Lacking Vimentin. Role of Endothelin-nitric Oxide Imbalance," J. Clin. Invest 100(6):1520-8, Sep. 15, 1997.

Terzi, F., et al., "Normal Tubular Regeneration and Differentiation of the Post-ischemic Kidney in Mice Lacking Vimentin," Am. J. Pathol. 150(4):1361-71, Apr. 1997.

Teixeira, V., et al., "Integrin Linked Kinase (ILK) Regulates Podocyte Phnotype in Vitro," Kidney & Blood Pressure Research 22(4-6):400, 1999.

Vielhauer, V., et al., "Obstructive Nephropathy in the Mouse: Progressive Fibrosis Correlates with Tubulointerstitial Chemokine Expression and Accumulation of CC Chemokine Receptor 2- and 5-positive Leukocytes," J. Am. Soc. Nephrol. 12(6):1173-87, Jun. 2001.

von Luttichau, I., et al., "Identification of a Signal Transduction Pathway that Regulates MMP-9 mRNA Expression in Glomerular Injury," Biol Chem. 383(7-8):1271-5, Jul.-Aug. 2002.

Wang, Y., et al., "Progressive Adriamycin Nephropathy in Mice: Sequence of Histologic and Immunohistochemical Events," Kidney Int. 58(4):1797-804, Oct. 2000.

Wanke, R., et al., "Accelerated Growth and Visceral Lesions in Transgenic Mice Expressing Foreign Genes of the Growth Hormone Family: An Overview," Pediatr Nephrol. 5(4):513-21, Jul. 1991.

Wu, C., et al., "Integrin-linked Protein Kinase Regulates Fibronectin Matrix Assembly, E-cadherin Expression, and Tumorigenicity," J. Biol. Chem. 273(1):528-36, Jan. 2, 1998.

ILK INHIBITORS FOR THE TREATMENT OF RENAL DISEASE

CROSS-REFERENCE TO RELATED APPLICATION

This application is a divisional of U.S. patent application Ser. No. 10/497,285, filed Jan. 4, 2005; which is a U.S. National Stage of PCT/CA02/01819 filed Nov. 26, 2002; which claims the benefit of U.S. Provisional Application No. 60/335,130, filed Nov. 30, 2001; all of these applications are incorporated herein by reference in their entireties.

BACKGROUND

1. Technical Field

The invention relates to the treatment of renal diseases using modulators of integrin linked kinase.

Progressive renal disease is an increasingly common and economically burdensome disease. A significant portion of patients progress to acute renal failure, a life threatening illness whose mortality has remained high despite the introduction of its only nonsurgical treatment, hemodialysis, about 25 years ago. Conventional hemodialysis mimics the filtration function of the kidneys by circulating a patient's blood through or over a dialysate solution physically separated from the blood by a porous or permeable wall or membrane. The process results in the preferential diffusion of small molecules, such as urea, from the bloodstream into the dialysate solution.

Although dialysis has dramatically changed the prognosis of renal failure, it is not a complete replacement therapy, since it only provides filtration function and does not replace the homeostatic, regulatory, and endocrine functions of the kidney. Patients on dialysis continue to have major medical problems.

In the United States, kidney failure is experienced by more than 360,000 people who depend on dialysis or a kidney transplant to survive. The number of people with kidney failure has actually doubled over the past 10 years, and the pool of candidates is large. Conservatively estimated, 10.9 million Americans have kidney disease and face the possibility of a future on dialysis or with a kidney transplant. Even with these remarkable treatments, nearly 58,000 people with kidney failure died in 1997. Jones, C. A., et al., Serum creatinine levels in the US population: third national health and nutrition examination survey. American Journal of Kidney Diseases, vol. 32, no. 6, pp. 992-999, December 1998.

Chronic renal failure may result from any major cause of renal dysfunction. The most common cause of end-stage renal disease is diabetic nephropathy, followed by hypertensive nephroangiosclerosis and various primary and secondary glomerulopathies. Plasma concentrations of creatinine and urea (which are highly dependent on glomerular filtration) begin a nonlinear rise as the renal function diminishes. Changes in creatinine and urea concentrations are minimal early on; later levels increase rapidly and are usually associated with systemic manifestations. For substances that are excreted mainly through distal nephron secretion, e.g., K, adaptation usually produces a normal plasma concentration until advanced failure occurs.

Kidney function depends on an intact glomerular filtration unit, allowing the excretion of potentially hazardous small molecular substances but retaining essential macromolecules. The permselectivity of the glomerular filter is defined by a fenestrated endothelial cell layer, the glomerular basement membrane (GBM), and podocytes. The podocyte forms the filtration slit, an ultrastructural membrane bridging the delicate web of interdigitating podocyte foot processes.

In glomerular disease there is progressive podocyte damage and proteinurea. Although the mechanisms for the progression of renal impairment remain fully undetermined, available evidence indicate that renal glomerular hypertension is responsible in part for the development of renal injury. In renal disease, afferent arteriolar tone is reported to be reduced, while the augmented intrarenal angiotensin II serves to act as an efferent arteriolar constrictor, both of which result in an increase in glomerular capillary pressure. Angiotensin converting enzyme inhibitors (ACE-I) are established as the agent possessing both antihypertensive and renoprotective actions, which exert vasodilator action on efferent arterioles. Calcium antagonists are also reported to have salutary effect on renal disease, although their beneficial action varies depending on the antagonists used and the underlying disease. Chronic progression can be slowed for 6-12 months using these drugs, but there is no other treatment at this time besides dialysis and ultimately transplantation of the organ.

A long-term replacement therapy which replaces all of the functions of the kidney and which is less costly than current dialysis therapies is desirable.

2. Description of the Related Art

Integrin-linked kinase (ILK) is a receptor-proximal protein kinase regulating integrin-mediated signal transduction. The ILK sequence is described in U.S. Pat. No. 6,013,782, herein incorporated by reference. The presence of ILK mRNA in proteinurea models and puromycin-induced podocyte damage is disclosed by Teixeira et al. (2000) Kidney & Blood Pressure Research 23(3-5):231; Unschuld et al. (1999) Kidney & Blood Pressure Research 22(4-6):400; Kretzler et al. (1998) Kidney & Blood Pressure Research 21(2-4):145. The distribution and regulation of ILK in normal and diabetic kidneys is discussed by Guo et al. (2001) Am J Pathol 159: 1735-1742.

BRIEF SUMMARY

The invention provides therapeutic compositions and methods for treatment of renal disease, specifically for modulating the activity of integrin linked kinase (ILK) to ameliorate glomerular renal disease states that may result in proteinuria, or states characterized by tubular or tubulo-interstitial damage. Treatment includes the administration of agents that interfere with the ILK signaling pathway, including integrin linked kinase (ILK) blocking agents; compounds that otherwise prevent the binding of natural ILK ligands to ILK; or compounds that prevent expression of, or signaling through, ILK. Such a treatment is used alone as single therapy or in combination with a second therapy as an adjunct to prevent, to reduce or to reverse the renal function.

DETAILED DESCRIPTION

In the subject methods, compounds that modulate the activity of integrin linked kinase (ILK) are administered systemically or locally to treat renal diseases, particularly those with underlying glomerular insufficiency, or tubular damage or insufficiency. Such a treatment is used alone as single therapy or in combination with a second therapy, including administration of angiotensin converting enzyme inhibitors as an adjunct to prevent, to reduce or to reverse the loss of renal function.

Animal and human proteinuric glomerulopathies evolve to terminal renal failure by a process leading to progressive parenchymal damage, which is relatively independent of the initial insult. The amount of urinary proteins, or proteinuria, correlates with the tendency of a given disease to progress. A constant feature of proteinuric nephritis is also the concomitant presence of tubulointerstitial inflammation. Biochemical events associated with tubular cell activation in response to protein stress include up-regulation of inflammatory and vasoactive genes such as MCP-1 and endothelins. The corresponding molecules formed in an excessive amount by renal tubuli are secreted toward the basolateral compartment of the cell and give rise to an inflammatory reaction that in most forms of glomerulonephritis consistently precedes renal scarring.

Causes of chronic renal failure include, without limitation, glomerulopathies, e.g., IgA nephropathy, focal glomerulosclerosis, membranous nephropathy, membranoproliferative glomerulonephritis, idiopathic crescentic glomerulonephritis, diabetes mellitus, postinfectious glomerulonephritis, systemic lupus erythematosus, Wegener's granulomatosis, hemolytic-uremic syndrome, amyloidosis; chronic tubulointerstitial nephropathies; hereditary nephropathies, e.g., polycistic kidney disease, Alport's syndrome, medullary cystic disease, Nail-patella syndrome; hypertension, e.g., nephroangiosclerosis, malignant glomerulosclerosis; renal macrovascular disease; and obstructive uropathy, e.g., ureteral obstruction, vesicoureteral reflux, benign prostatic hyperplasia; and the like.

Chronic renal failure (CRF) may result from any major cause of renal dysfunction. The functional effects of CRF can be categorized as diminished renal reserve, renal insufficiency (failure), and uremia. Plasma concentrations of creatinine and urea begin a nonlinear rise as the renal function diminishes. Na and water balance is well maintained by increased fractional excretion of Na and a normal response to thirst. Thus, the plasma Na concentration is typically normal and hypervolemia is infrequent despite unmodified dietary intake of Na. However, imbalances may occur if Na and water intakes are very restricted or excessive.

Patients with mildly diminished renal reserve are asymptomatic, and renal dysfunction can be detected only by laboratory testing. A patient with mild to moderate renal insufficiency may have only vague symptoms despite elevated BUN and creatinine; nocturia is noted, principally due to a failure to concentrate the urine during the night. Lassitude, fatigue, and decreased mental acuity often are the first manifestations of uremia.

Neuromuscular features include coarse muscular twitches, peripheral neuropathies with sensory and motor phenomena, muscle cramps, and convulsions. Anorexia, nausea, vomiting, stomatitis, and an unpleasant taste in the mouth are almost uniformly present. In advanced CRP, GI ulceration and bleeding are common. Hypertension is present in >80% of patients with advanced renal insufficiency and is usually related to hypervolemia and occasionally to activation of the renin-angiotensin-aldosterone system. Cardiomyopathy and renal retention of Na and water may lead to congestive heart failure or dependent edema. Pericarditis, usually seen in chronic uremia, may occur in acute, potentially reversible, uremia. Abnormalities with lipid metabolism also occur with CRF, on dialysis, and after renal transplantation. The primary finding in CRF and dialysis is hypertriglyceridemia; the total cholesterol level is usually normal.

Treatments useful as an adjunct to the present methods include diet for controlling hyperglycemia in diabetic nephropathy and hypertension, and protein restriction. Administration of ACE inhibitors, and angiotensin receptor blockers is also of interest.

ILK Modulating Agents

ILK is a 59 kDa serine/threonine kinase that associates with the cytoplasmic tails of β1 and β3 integrins. The enzymatic activity for ILK is modulated by the interaction of cells with the extracellular matrix component fibronectin, integrin clustering and a number of growth factors. Because of its intimate association with a wide variety of signaling pathways that have been directly or indirectly implicated in various pathological processes, ILK may represent a therapeutic target for a variety of clinical conditions including angiogenesis, cancer, inflammation and autoimmunity. The genetic sequence of human ILK is disclosed in U.S. Pat. Nos. 6,013, 782; and 6,001,622, herein incorporated by reference.

Agents that block ILK activity are used in the treatment of renal disease relating to neovascularization. Numerous agents are useful in reducing ILK activity, including agents that directly modulate ILK expression, e.g., anti-sense specific for ILK, ILK specific antibodies and analogs thereof, small organic molecules that block ILK catalytic or binding activity, etc.; and agents that affect ILK activity through direct or indirect modulation of [PtdIns(3,4,5)$P_3$] levels in a cell. For example, small molecule inhibitors of integrin linked kinase are described in U.S. Pat. No. 6,214,813. Antisense inhibitors of ILK are described in U.S. Pat. No. 6,177,273, each herein incorporated by reference.

Agents of interest for down-regulating ILK activity include direct blocking of [PtdIns(3,4,5)$P_3$] binding sites through competitive binding, steric hindrance, etc. Of particular interest are antibodies that bind to the PH domains, thereby blocking the site. Antibodies include fragments, e.g., F(Ab), F(Ab)′, and other mimetics of the binding site. Such antibodies can be raised by immunization with the protein or the specific domain. Mimetics are identified by screening methods. Analogs of [PtdIns(3,4,5)$P_3$] that compete for binding sites but do not result in activation of ILK are also of interest.

Because ILK activity is upregulated by the presence of the lipid [PtdIns(3,4,5)$P_3$], the activity of ILK can be manipulated by agents that affect cellular levels of [PtdIns(3,4,5)$P_3$], or that block the binding of [Ptdins(3,4,5)$P_3$] to ILK. The amino acid sequence of ILK contains a sequence motif found in pleckstrin homology (PH) domains, which are involved in the binding of phosphatidylinositol phosphates. The activity of ILK is also down-regulated by inhibiting the activity of PI(3) kinase, thereby decreasing cellular levels of [PtdIns(3, 4,5)$P_3$]. Agents of interest include inhibitors of PI(3) kinase, e.g., wortmannin, LY294002, etc. Physiologically effective levels of wortmannin range from about 10 to 1000 nM, usually from about 100 to 500 nM, and optimally at about 200 nM. Physiologically effective levels of LY294002 range from about 1 to 500 μM, usually from about 25 to 100 gM, and optimally at about 50 μM. The inhibitors are administered in vivo or in vitro at a dose sufficient to provide for these concentrations in the target tissue.

Drug screening can be used to identify agents that modulate ILK function. One can identify ligands or substrates that inhibit the action of ILK. A wide variety of assays may be used for this purpose, including labeled in vitro protein-protein binding assays, electrophoretic mobility shift assays, immunoassays for protein binding, and the like. Knowledge of the 3-dimensional structure of ILK, derived from crystallization of purified recombinant ILK protein, leads to the rational design of small drugs that specifically inhibit ILK activity. These drugs may be directed at specific domains of ILK, e.g., the kinase catalytic domain, ankyrin repeat domains, pleckstrin homology domains, etc. Among the agents of interest for drug screening are those that interfere with the binding of cytoplasmic integrin tails to ILK; the kinase activity of ILK; binding of [Ptdins(3,4,5)P$_3$] to the PH domains of ILK and agents that inhibit the production of [PtdIns(3,4,5)P$_3$] by P1 (3) kinase.

The term "agent" as used herein describes any molecule, e.g., protein or pharmaceutical, with the capability of altering the physiological function of ILK. Candidate agents encompass numerous chemical classes, though typically they are organic molecules, preferably small organic compounds having a molecular weight of more than 50 and less than about 2,500 daltons. Candidate agents comprise functional groups necessary for structural Interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of interest may detect agents that block ILK function, such as integrin binding, kinase activity, down regulation of E-cadherin, up regulation of LEF-1, binding properties, etc. For example, an expression construct comprising an ILK gene may be introduced into a cell line under conditions that allow expression. The level of ILK activity is determined by a functional assay, as previously described. In one screening assay, candidate agents are added, and the formation of fibronectin matrix is detected. In another assay, the ability of candidate agents to enhance ILK function is determined.

Methods of Treatment

The subject methods are used for prophylactic or therapeutic purposes to treat renal diseases, particularly to prevent, reduce or reverse the loss of glomerular function. As used herein, the term "treating" is used to refer to both prevention of disease, and treatment of pre-existing conditions. While treatment during early stages is desirable, the adverse symptoms of the disease may be at least partially alleviated by treatment during later stages.

Suitable animal models exist for determination of an effective dose of an ILK inhibitor, for example as set forth in the examples. However the efficacy of a therapeutic effect for different mammals varies widely; for example, doses typically are 20, 30 or even 40 times smaller (per unit body weight) in man than in the rat. Similarly the mode of administration can have a large effect on dosage. Formulation or treatment with an adjunct therapeutic agent or regimen may also affect the effective dose In practicing the method of treatment or use of the present invention, a therapeutically effective amount of an ILK inhibitor is administered to a subject afflicted with a disease or disorder related to loss of renal function, particularly to glomerular insufficiency relating to progressive podocyte damage and proteinurea. The inhibitor may be administered in accordance with the method of the invention either alone or in combination with other known therapies. When co-administered with one or more other therapies, the inhibitor may be administered either simultaneously with the other treatment(s), or sequentially. If administered sequentially, the attending physician will decide on the appropriate sequence of administration, which may be before or after a second therapy.

In addition to dietary management, administration of ACE inhibitors is useful as adjunct therapy. ACE inhibitor include, but are not limited to, captopril, benazeprile, enalapril, fosinopril, lisinopril, quinapril, Ramipril, imidapril, perindopril, erbumine, and trandolapril. ACE receptor blockers may also be used in place of or as well as ACE inhibitors, and these include losartan, irbesartan, candesartan, cilexetil, and valsartan.

The dose of ILK inhibitor in the pharmaceutical composition of the present invention will depend upon the nature and severity of the condition being treated, and on the nature of prior treatments which the patent has undergone. Ultimately, the attending physician will decide the dose with which to treat each individual patient. Initially, the attending physician may administer low doses and observe the patient's response. Larger doses may be administered until the optimal therapeutic effect Is obtained for the patient, and at that point the dosage is not increased further.

The compounds of this invention can be incorporated into a variety of formulations for therapeutic administration. Administration of an ILK inhibitor may be by delivery using any appropriate means including, but not limited to, systemic, local, or even direct application to the target tissue. Local delivery of an ILK inhibitor provides a high local concentration while reducing the likelihood of non-specific anti-angiogenic or other undesirable side effects that may follow systemic administration of an ILK inhibitor.

The compounds of the present invention are formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The ILK may be systemic after administration or may be localized by the use of an implant that acts to retain the active dose at the site of implantation.

The compounds of the present invention can be administered alone, in combination with each other, or they can be used in combination with other known compounds and therapies. In pharmaceutical dosage forms, the compounds may be administered in the form of their pharmaceutically acceptable salts, or they may also be used alone or in appropriate association, as well as in combination with other pharmaceutically active compounds.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of Infection, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which scope will be determined by the language in the claims.

It must be noted that as used herein and in the appended claims, the singular forms "a", "and", and "the" include plural referents unless the context clearly dictates otherwise. Thus, for example, reference to "a subject" includes a plurality of such subjects and reference to "the receptor" includes reference to one or more receptors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for all relevant purposes, e.g., the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

In the examples, "ILK inhibitor" may mean antisense, peptides, antibodies, or small molecule inhibitors. Small molecule inhibitors of ILK are exemplified in U.S. Pat. No. 6,214,813, which is hereby incorporated by reference.

Example 1

ILK Inhibition as Therapeutic Interventions

Methods

Mice transgenic for the bovine growth hormone (GH) under a methallothionein I promoter were used (Wanke, R. et al., Pediatric Nephrol (1991) 5:513-521). Genotype was confirmed by genomic PCR with bovine GH specific primers (Wanke et al. 1991). Glomeruli were isolated after pooling kidneys from two animals.

For the animal model, accelerated nephrotoxic serum nephritis (NTX) was induced in 4 to 6 week old females as previously reported (Schadde et al. Nephrol Dial Transplant (2000) 15:1046-1053; Neugarten et al. J Am Soc Nephrol (1995) 5:1903-1909).

Five days after preimmunization with rabbit IgG, 400 μg of a protein A purified IgG fraction of a nephrotoxic rabbit anti-murine GBM antiserum was intravenously injected, controls received carrier only. Mice In each group were sacrificed after 0, 2, and 7 days and a pooled glomerular fraction was obtained from each group for expression analysis. Albuminuria was determined using a commercially available mouse albumin specific ELISA system (Exocell, Philadelphia, Pa.).

Measuring Levels of ILK from Podocytes. To assess the efficacy of ILK inhibiting agents in vivo, the podocyte extraction method may be used. Single cell RT-PCR was performed as described in Schroppel et al. Kidney Int (1998) 53:119-124. Freshly dissected glomeruli from CD-1 mice were transferred to a patch clamp apparatus. Single podocytes were selectively harvested by aspiration of the cells into a micropipette, reverse transcribed and RT-PCR was performed essential as described above, but using 60 instead of 30 cycles. Perfusion medium aspirated next to a glomerulus was processed in parallel and served as negative control. Single cell ILK RT-PCR product identity was verified by restriction digest. Single podocyte RNA was quantified using published real-time RT PCR technology (Heid et al. Genome Res (1996) 6:986-994). For determination of ILK copy number per single podocyte cDNA a standard curve of serial dilutions of ILK plasmid cDNA with known copy numbers was employed. ILK copies per podocyte cDNA were calculated using the Ct value minus the dilution factor and the standard curve ($y=-1,6227Ln(x)+39$ with $R2=0,9935$) generated from duplicate amplification reactions of log fold dilutions between 100,000 and 10 ILK plasmid copies.

In vitro podocytes model. As an in vitro model system conditionally immortalized podocytes were used (Mundel et al. Exp Cell Res (1997) 236, 248-256). Cells were propagated under permissive conditions at 33° C. with RPMI 1640 medium (Life Technologies) supplemented with 10% FCS (Bio Whittaker, Verviers, Belgium), 100 U/ml penicillin, 100 mg/ml streptomycin and 10 U/ml mouse recombinant interferon-γ (Sigma). To induce differentiation, podocytes were maintained on type I-collagen (Biochrom, Berlin, FRG) coated surface at 37° C. without interferon-g (non-permissive conditions) for at least 8 days. Cells at passage 12-24 were used. Mouse mesangial cells were employed in control experiments. For our studies, 90-day-old mice with severe albuminuria were employed. Wildtype littermates served as controls. Six to eight animals in each group were analyzed.

| GROUP | ANIMAL TYPE | TREATMENT |
| --- | --- | --- |
| Negative control group: | Wildtype litter mates, week 6-12 of disease progression | Carrier only |
| Positive control group | GH-transgenic mice, week 6-12 of disease progression | Carrier only |
| Test animals | GH-TX mice | Various doses of ILK inhibitor weeks 6-12 |
| Test animals | GH-TX mice | Various doses of ILK inhibitor for full 12 weeks. |

ILK inhibitors are administered orally, intraperitoneally or by subcutaneous infusion pump, in daily doses ranging from 0.01-200 mg/kg. Vehicle (carrier) controls are administered in equivalent volumes by the same routes. Experimental readouts included albuminuria, serum urea, histology and gene expression profiles.

Negative control mice demonstrate no significant changes in experimental readouts. The positive control group demonstrate significant changes associated with progressive renal glomerulosclerosis in histology and biochemical readouts. In the experimental GH TX groups treated with various doses of ILK inhibitor, significant decreases in measured parameters of progressive renal glomerulosclerosis are demonstrated compared to the positive control group, indicating that administration of ILK inhibitors results in therapeutic benefit in this model of progressive renal disease.

Example 2

Adriamycin-Induced Proteinuria

This model, which results In focal glomerular sclerosis (FGS), is described in Wang et al. Kidney Int (2000) 58:1797-1804. Groups of BALB/c mice are injected intravenously on days 0 and 14 with Adriamycin (ADR, doxorubicin hydrochloride, Pharmacia & Upjohn) at 10-13 mg/kg, or vehicle control. Six to eight animals in each group are analyzed.

| GROUP | TREATMENT |
| --- | --- |
| Negative control group | Intravenous carrier on day 0 & 14, vehicle daily from day 0 |
| Positive control group | Intravenous ADR on day 0 & 14, vehicle daily from day 0 |
| Test group | Intravenous ADR on day 0 & 14, various doses of ILK inhibitor from day 0 |

ILK inhibitors are administered orally, intraperitoneally or by subcutaneous infusion pump, in daily doses ranging from 0.01-200 mg/kg, beginning on day 0. Vehicle (carrier) controls are administered in equivalent volumes by the same routes. Experimental readouts include weekly body weight, urine volume, urinary protein, serum creatinine and albumin, and terminal histopathology.

Negative control mice demonstrate no significant changes in experimental readouts. The positive control group demonstrate significant changes associated with rapid progressive renal disease (FGS) using experimental readouts, namely proteinuria, hypoalbuminemia, hypercreatininemia, and progressive renal injury by histology. In the experimental groups treated with various doses of ILK inhibitor, significant decreases in measured parameters of progressive renal disease are demonstrated compared to the positive control group, indicating that administration of ILK inhibitors results in therapeutic benefit in this model of acute progressive focal glomerular sclerosis.

Example 3

Murine Unilateral Uretheral Obstruction

This model results in epithelial-mesenchymal transdifferentiation in renal fibrosis and is described in Vielhauer et al. J Am Soc Nephrol (2001) 12: 1173-1187. Briefly, female inbred C57BL/6 mice weighing 20-26 g were obtained and kept under a 12-h light/dark cycle. Food and water were available ad libitum. Under general anesthesia, unilateral ureteral ligation resulting in UUO was performed by ligating the left distal ureter with a 2/0 Mersilene suture through a low midline abdominal incision. Unobstructed contralateral kidneys served as controls.

| GROUP (8-10 mice) | PRE-TREATMENT | TREATMENT |
| --- | --- | --- |
| Negative control group | Sham operated mice | Receive carrier only for ten days |
| Positive control group | Mice with one obstructed kidney | Receive carrier only for ten days |
| Test group | Mice with one obstructed kidney | Receive various doses of ILK inhibitor for ten days |

ILK inhibitors are administered orally, intraperitoneally or by subcutaneous infusion pump, in daily doses ranging from 0.01-200 mg/kg. Vehicle (carrier) controls are administered in equivalent volumes by the same routes. Experimental readouts included histological fibrosis scores, serum urea, collagen levels and ILK mRNA expression. Analysis of ILK mRNA levels are also performed in infiltrating cells (macrophages and T-cells) after cell sorting in renal fibrosis in the UUO model.

Negative control (sham operated) mice demonstrated no significant changes in experimental readouts. The UUO control group demonstrated significant changes associated with renal fibrosis in the ligated kidney using experimental readouts. Also observed in these animals was a fourfold ILK mRNA induction.

In the experimental groups treated with various doses of ILK inhibitor, the non-ligated kidneys are used as internal controls, the non-ligated kidneys demonstrated no significant changes associated with renal tubulo-interstitial fibrosis using experimental readouts; however, the damaged kidneys demonstrated significant decreases in measured parameters of renal fibrosis compared to the UUO control group. These results indicate that administration of ILK inhibitors results in therapeutic benefit in this model of renal tubulo-interstitial fibrosis.

Example 4

Preparation of DNA Oligonucleotides and RNA Transcripts

Antisense molecules can be used to inhibit the activity of ILK to treat disease. Phosphodiester oligodeoxynucleotides were produced on an Applied Biosystems 394 synthesizer using standard phosphoramidite chemistry. In vitro RNA transcripts of ILK cDNA were produced with the Promega RiboMax Large Scale RNA Production System T7 and cDNA template derived from the plasmid ILK13/pRC/CMV (Hannigan et al. Nature (1996) 379:91-96) linearized at Xba I. The crude RNA transcript was purified using a Qiagen RNeasy mini spin kit.

Antisense molecules are administered intravenously, intraperitoneally, orally or intralumenally, and may be formulated in pharmaceutically acceptable carriers such as lipids, liposomes, polymers, or saline.

REFERENCES

Adler, S., R. Sharma, V. J. Savin, R. Abbi, and B. Eng. (1996) Alteration of glomerular permeability to macromolecules induced by cross-linking of beta 1 integrin receptors. Am J Pathol. 149:987-996.

Bariety J, Nochy D, Mandet C, Jacquot C, Glotz D, Meyrier A (1998) Podocytes undergo phenotypic changes and express macrophagic-associated markers in idiopathic collapsing glomerulopathy. Kidney Int 53:4 918-25

Bariety J, Bruneval P, Hill G, Irinopoulou T, Mandet C, Meyrier A (2001) Posttransplantation relapse of FSGS is characterized by glomerular epithelial cell transdifferentiation. J Am Soc Nephrol 12:2 261-74, Route, N., O. Gribouval, S. Roselli, F. Benessy, H. Lee, A. Fuchshuber, K. Dahan, M. Gubler, P. Niaudet, and C. Antignac. (2000) NPHS2, encoding the glomerular protein podocin, is mutated in autosomal recessive steroid-resistant nephrotic syndrome. Nature Genetics. 24:349-354.

Coimbra T M, Janssen U, Grone H J, Ostendorf T, Kunter U, Schmidt H, Brabant G, Floege J (2000) Early events leading to renal injury in obese Zucker (fatty) rats with type II diabetes. Kidney Int 2000 January 57:1 167-82

Colucci-Guyon E, Portier M M, Dunia I, Paulin D, Poumin S, Babinet C (1994) Mice lacking vimentin develop and reproduce without an obvious phenotype. 79:4 679-94.

Guo, L., Sanders Paul W., Woods, A., and Wu, Chuanyue (2001) The distribution and regulation of integrin-linked kinase in normal and diabetic kidneys. Am J Pathol 159: 1735-1742

Haltia, A., M. Solin, P. Luimula, M. Kretzler, and H. Holthofer. (1999) mRNA differential display analysis of nephrotic kidney glomeruli. Exp Nephrol. 7:52-58.

Hannigan, G. E., C. Leung-Hagesteijn, L. Fitz-Gibbon, M. G. Coppolino, G. Radeva, J. Filmus, J. C. Bell, and S. Dedhar. (1996) Regulation of cell adhesion and anchorage-dependent growth by a new beta 1-integrin-linked protein kinase. Nature. 379:91-96.

Held, C. A., J. Stevens, K. J. Livak, and P. M. Williams. (1996) Real time quantitative PCR. Genome Res. 6:986-994.

Huttunen, N. P., N. Hallman, and J. Rapola. (1976) Glomerular basement membrane antigens in congenital and acquired nephrotic syndrome in childhood. Nephron. 16:401-414.

Kaplan, J., S. Kim, K. North, H. Rennke, L. Correia, H. Tong, B. Mathis, J. Rodriguez-Perez, P. Allen, A. Beggs, and M. Pollak. (2000) Mutations in ACTN4, encoding alpha-actinin-4, cause familial focal segmental glomerulosclerosis. Nat Genet. 24:251-256.

Kestilä, M., U. Lenkkeri, M. Männikkö, J. Lamerdin, P. McCready, H. Putaala, V. Ruotsalainen, T. Morita, M. Nissinen, R. Herva et al. (1998) Positionally cloned gene for a noval glomerular protein-nephrin- is mutated in congenital nephrotic syndrome. Molecular Cell. 1:575-582.

Kreidberg, J. A., M. J. Donovan, S. L. Goldstein, H. Rennke, K. Shepherd, R. C. Jones, and R. Jaenisch. (1996) Alpha 3 beta I integrin has a crucial role in kidney and lung organogenesis. Development. 122:3537-3547.

Kretzler, M., G. Fan, D. Rose, L. Arend, J. Briggs, and L. Holzman. (1996) Identification of novel mouse embryonic renal marker gene products differentially expressed during kidney development. Am J Physiol (Renal Fluid Electrolyte Physiol 40). 271:F770-777.

Kretzler, M.; Holthofer, H.; Unschuld, K. G.; Wanke, R.; Mundel, P.; Schloendorff, D. (1998) Kidney & Blood Pressure Research 21 (2-4):145

Mundel P, Reiser J, Zuniga Mejia Borja A, Pavenstadt H, Davidson G R, Kriz W, Zeller R. (1997) Rearrangements of the cytoskeleton and cell contacts induce process formation during differentiation of conditionally immortalized mouse podocyte cell lines. Exp Cell Res 236(1):248-58

Neugarten, J., G. W. Feigth, K. J. Assmann, Z. Shan, E. R. Stanley, and D. Schlondorff. (1995) Role of macrophages and colony-stimulating factor-1 in murine antiglomerular basement membrane glomerulonephritis. J Am Soc Nephrol. 5:1903-1909.

Novak, A., S. C. Hsu, C. Leung-Hagesteijn, G. Radeva, J. Papkoff, R. Montesano, C. Roskelley, R. Grosschedl, and S. Dedhar. (1998) Cell adhesion and the integrin-linked kinase regulate the LEF-1 and beta-catenin signaling pathways. Proc Natl Acad Sci USA. 95:4374-4379.

O'Meara, Y. M., M. W. M., D. J. Goldstein, and D. J. Salant. (1991) Nephrotoxic antiserum identifies a 131 integrin on rat glomerular epithelial cells. J Am Soc Nephrol. 2:580 (Abstr.).

Radeva, G., T. Petrocelli, E. Behrend, C. Leung-Hagesteijn, J. Filmus, J. Slingerland, and S. Dedhar. (1997) Overexpression of the integrin-linked kinase promotes anchorage-independent cell cycle progression. J Biol Chem. 272: 13937-13944.

Sanai T, Sobka T, Johnson T, el-Essawy M, Muchaneta-Kubara E C, Ben Gharbia O, el Oldroyd S, Nahas A M (2000) Expression of cytoskeletal proteins during the course of experimental diabetic nephropathy. Diabetologia 43:191-100

Schadde, E., M. Kretzler, B. Banas, B. Luckow, K Assmann, and D. Schlondorff. (2000) Expression of chemokines and their receptors in nephrotoxic serum nephritis. Nephrol Dial Transplant. 15:1046-1053.

Schroppel, B., S. Huber, M. Horster, D. Schlondorff, and M. Kretzler. (1998) Analysis of mouse glomerular podocyte mRNA by single-cell reverse transcription-polymerase chain reaction. Kidney Int. 53:119-124.

Shankland, S. J., F. Eitner, K. L. Hudkins, T. Goodpaster, V. D'Agati, and C. E. Alpers. (2000) Differential expression of cyclin-dependent kinase inhibitors in human glomerular disease: Role in podocyte proliferation and maturation. Kidney Int. 58:674683.

Teixeira, V P C., Schlondorff, D.; Kretzler, M., Mundel, P. et al. (2000) Kidney & Blood Pressure Research 23(3-5): 231.

Terzi F, Maunoury R, Colucci-Guyon E, Babinet C, Federici P, Briand P, Friedlander G. (1997) Normal tubular regeneration and differentiation of the post-ischemic kidney in mice lacking vimentin. Am J Pathol 50:4 1361.71

Terzi F, Henrion D, Colucci-Guyon E, Federici P, Babinet C, Levy B I, Briand P, Friedlander G (1997) Reduction of renal mass is lethal in mice lacking vimentin. Role of endotheliri-nitric oxide imbalance. J Clin Invest 100:6 1520-8

Unschuld, P. G.; Teixeira, VPC.; Schloendorff, D.; Kretzler, M.; Edenhofer, I.; Holthoefer, H.; Mundel, P. (1999) Kidney & Blood Pressure Research 22 (4-6):400.

Vielhauer V, Anders H J, Mack M, Cihak J, Strutz F, Stangassinger M, Luckow B, Grone H J, Schlondorff D. (2001) Obstructive nephropathy in the mouse: progressive fibrosis correlates with tubulointerstitial chemokine expression and accumulation of CC chemokine receptor 2- and 5-positive leukocytes. J Am Soc Nephrol 12(6):1173-87

Wang Y, Wang Y P, Tay Y C, Harris D C. (2000) Progressive adriamycin nephropathy in mice: sequence of histologic and immunohistochemical events. Kidney Int 58(4):1797-1804

Wanke, R., W. Hermanns, S. Folger, J. Ehrlein, E. Wolf, and G. Brem. (1991) Accelerated growth and visceral lesions in transgenic mice expressing foreign genes of the growth hormone family. Pediatr Nephrol. 5:513-521.

Wu, C., S. Y. Keightley, C. Leung-Hagesteijn, G. Radeva, M. Coppolino, S. Goicoechea, J. A. McDonald, and S. Dedhar. (1998) Integrin-linked protein kinase regulates fibronectin matrix assembly, E-cadherin expression, and tumorigenicity. J Biol Chem. 273:528-536.

Kretzler M, Teixeira V P, Unschuld P G, Cohen C D, Wanke R, Edenhofer I, Mundel P, Schlondorff D, Holthofer H (2001) Integrin-linked kinase as a candidate downstream effector in proteinuria. FASEB J 15:10 1843-5

The invention claimed is:

1. A method for treating a patient with renal dysfunction, the method comprising:
   administering an effective dose of an integrin linked kinase (ILK) inhibitor to said patient.

2. The method according to claim 1, wherein said ILK inhibitor is a nucleic acid.

3. The method according to claim 2, wherein said nucleic acid is an antisense molecule specific for ILK.

4. The method of claim 1, wherein said ILK inhibitor is a peptide.

5. The method of claim 1, wherein said ILK inhibitor is a small molecule of between 250 Daltons and 1000 Daltons molecular weight.

6. The method of claim 1, wherein said ILK inhibitor is an antibody or antibody fragment.

7. The method of claim 1, further comprising administering an ACE inhibitor to said patient.

8. The method of claim 1, wherein the renal dysfunction comprises glomerular insufficiency.

9. The method of claim 1, wherein the renal dysfunction comprises tubular damage or insufficiency.

10. The method of claim 1, wherein the renal dysfunction is chronic renal failure caused by one or more of the following:
    glomerulopathy, chronic tubulointerstitial nephropathy, hereditary nephropathy, hypertension, nephroangiosclerosis, malignant glomerulosclerosis, renal macrovascular disease, obstructive uropathy and diabetic nephropathy.

11. The method of claim 10 wherein the glomerulopathy comprises IgA nephropathy, focal glomerulosclerosis, membraneous nephropathy, membranoproliferative glomerulonephritis, idiopathic crescentic glomerulonephritis, diabetes mellitus, postinfectious glomerulonephritis, systemic lupus erythematosus, Wegener's granulomatosis, hemolytic-uremic syndrome, or amyloidosis.

12. The method of claim 10 wherein the hereditary nephropathy comprises polycystic kidney disease, Alport's syndrome, medullary cystic disease or Nail-patella syndrome.

13. The method of claim 10 wherein the obstructive uropathy comprises ureteral obstruction, vesicoureteral reflux or benign prostatic hyperplasia.

14. The method of claim 1 wherein the ILK inhibitor is administered daily to the patient in a dose ranging from 0.01 mg/kg to 200 mg/kg.

15. The method of claim 1 wherein the ILK inhibitor is administered to the patient orally, intraperitoneally or subcutaneously.

16. The method of claim 1 wherein the ILK inhibitor is formulated for sustained release administration.

17. A method for lowering protein levels in urine, the method comprising:
    administering an effective dose of an integrin linked kinase (ILK inhibitor to a patient with renal dysfunction.

18. The method according to claim 17, wherein said ILK inhibitor is a nucleic acid.

19. The method according to claim 18, wherein said nucleic acid is an antisense molecule specific for ILK.

20. The method of claim 17, wherein said ILK inhibitor is a peptide.

21. The method of claim 17, wherein said ILK inhibitor is a small organic compound.

22. The method of claim 17, wherein said ILK inhibitor is an antibody or antibody fragment.

23. The method of claim 17, further comprising administering an ACE inhibitor to said patient.

24. The method of claim 1, wherein said ILK inhibitor modulates ILK activity in the podocytes of the patient's kidney.

* * * * *

UNITED STATES PATENT AND TRADEMARK OFFICE
CERTIFICATE OF CORRECTION

PATENT NO. : 7,678,775 B2  Page 1 of 1
APPLICATION NO. : 11/855884
DATED : March 16, 2010
INVENTOR(S) : Matthias Kretzler et al.

It is certified that error appears in the above-identified patent and that said Letters Patent is hereby corrected as shown below:

Title Page, Item (75) Inventors:
"Patricia Logan, Vancouver, CA (US)" should read --Patricia Logan, Vancouver, BC (CA)--.

Column 14, Line 37:
"(ILK inhibitor to a patient with renal dysfunction" should read --(ILK) inhibitor to a patient with renal dysfunction--.

Signed and Sealed this

Fifth Day of October, 2010

David J. Kappos
*Director of the United States Patent and Trademark Office*